(12) United States Patent
Fang et al.

(10) Patent No.: US 8,931,125 B2
(45) Date of Patent: Jan. 13, 2015

(54) CRADLE DRIVE MECHANISM, A TABLE, AND A PATIENT IMAGING AND CARRYING APPARATUS

(71) Applicant: GE Medical Systems Global Technology Company, LLC., Waukesha, WI (US)

(72) Inventors: Xianfa Fang, Beijing (CN); Gaoxian Zhang, Beijing (CN); Gang Hu, Beijing (CN); Xin Yang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 323 days.

(21) Appl. No.: 13/628,700

(22) Filed: Sep. 27, 2012

(65) Prior Publication Data

US 2013/0081489 A1 Apr. 4, 2013

(51) Int. Cl.
| | | |
|---|---|---|
| *A47B 13/00* | (2006.01) | |
| *F16H 37/12* | (2006.01) | |
| *A61B 6/04* | (2006.01) | |
| *A61B 5/055* | (2006.01) | |
| *F16H 19/06* | (2006.01) | |

(52) U.S. Cl.
CPC ............ *F16H 37/124* (2013.01); *A61B 6/0471* (2013.01); *A61B 5/0555* (2013.01); *F16H 19/0604* (2013.01)
USPC ........... 5/601; 5/81.1 HS; 378/209; 74/89.34; 74/89.23; 74/89.45; 74/89.17; 74/37; 74/25; 74/29; 74/31; 74/33; 108/20; 108/137; 108/143

(58) Field of Classification Search
USPC ................. 5/601, 81.1 HS; 108/20, 137, 143; 74/25, 29, 31, 33, 35, 37, 89.23–89.45; 378/209
See application file for complete search history.

(56) References Cited

U.S. PATENT DOCUMENTS

| | | | | |
|---|---|---|---|---|
| 2,867,058 A | * | 1/1959 | Balsiger et al. ............... | 451/249 |
| 3,090,498 A | * | 5/1963 | Palmer .......................... | 414/728 |
| 3,174,634 A | * | 3/1965 | Peck ............................. | 414/541 |
| 3,588,500 A | * | 6/1971 | Koerner ........................... | 5/601 |
| 3,731,821 A | * | 5/1973 | Wallis .......................... | 414/753.1 |
| 3,889,818 A | * | 6/1975 | Wennerstrom ................ | 212/349 |
| 4,495,828 A | * | 1/1985 | Iwamoto ........................ | 74/110 |
| 4,590,380 A | * | 5/1986 | Tamaki .................... | 250/442.11 |
| 5,125,789 A | * | 6/1992 | Farr ............................... | 414/728 |

(Continued)

FOREIGN PATENT DOCUMENTS

JP 2010-57700 A 3/2010

*Primary Examiner* — Michael Trettel
*Assistant Examiner* — Ifeolu Adeboyejo
(74) *Attorney, Agent, or Firm* — Global Patent Operation; Mark A. Conklin

(57) ABSTRACT

A cradle drive mechanism is provided. The cradle drive mechanism includes a drive motor, an intermediate frame and a screw and nut transmission device driven by the drive motor so as to drive linear reciprocating motion of the intermediate frame. The cradle drive mechanism also includes a rotating shaft having a first driving wheel and a gear, a transmission belt, and a rack meshed with the gear so that, during linear reciprocating motion of the intermediate frame, the rack forces the gear to rotate and drive rotation of the first driving wheel, wherein rotation of the first driving wheel drives rotation of the transmission belt. The cradle drive mechanism also includes a cradle connector fixed on the transmission belt and configured to connect a cradle and to drive linear reciprocating motion of the cradle.

10 Claims, 4 Drawing Sheets

(56) References Cited

U.S. PATENT DOCUMENTS

| | | | |
|---|---|---|---|
| 5,199,123 A * | 4/1993 | Jacques et al. | 5/601 |
| 5,210,893 A * | 5/1993 | Uosaki et al. | 5/601 |
| 5,272,776 A * | 12/1993 | Kitamura | 5/601 |
| 5,808,468 A * | 9/1998 | Bis et al. | 324/318 |
| 6,499,159 B1 * | 12/2002 | Schmitt et al. | 5/601 |
| 6,615,428 B1 * | 9/2003 | Pattee | 5/601 |
| 6,615,429 B2 * | 9/2003 | Weil et al. | 5/601 |
| 6,955,464 B1 * | 10/2005 | Tybinkowski et al. | 378/209 |
| 7,430,772 B2 * | 10/2008 | Van Es | 5/601 |
| 7,437,785 B2 * | 10/2008 | Farooqui | 5/601 |
| 7,634,827 B2 * | 12/2009 | Gagneur et al. | 5/601 |
| 7,697,971 B1 * | 4/2010 | Green et al. | 600/415 |
| 7,742,562 B2 * | 6/2010 | Weber | 378/68 |
| 8,621,689 B2 * | 1/2014 | Dong et al. | 5/601 |
| 2007/0143921 A1 * | 6/2007 | Hiyama | 5/601 |
| 2008/0060133 A1 * | 3/2008 | Farooqui | 5/601 |
| 2008/0235874 A1 * | 10/2008 | Grosshauser et al. | 5/601 |
| 2009/0070935 A1 * | 3/2009 | Brunker et al. | 5/601 |

* cited by examiner

CRADLE DRIVE MECHANISM, A TABLE, AND A PATIENT IMAGING AND CARRYING APPARATUS

BACKGROUND OF THE INVENTION

The present application relates to the field of medical imaging apparatus, and more particularly, to a cradle drive mechanism, a table having such cradle drive mechanism and a patient imaging and carrying apparatus having such table.

Generally, a patient can be scanned and imaged by a variety of imaging techniques in order to make diagnosis Such imaging techniques can include magnetic resonance imaging (MRI), computer tomography (CT), X-ray imaging, positron emission tomography (PET) and the like. A patient imaging and carrying apparatus employing such imaging techniques generally includes a movable table so as to carry and position the patient accurately.

As shown in FIG. 1, a patient imaging and carrying apparatus employing the magnetic resonance imaging technique usually includes the following three portions: a table 21, an imaging system 22 and a rear pedestal 23. In this apparatus, the imaging system 22 is a magnetic resonance imaging system. The table 21 is movable, in order to get close to the imaging system 22. The table 21 can also move up and down so that the vertical position of the patient can be adjusted. The table 21 includes a cradle 24, and the cradle 24 can move relative to the table 21 in order to carry the patient into the magnet bore of the imaging system 22. When the front part of the cradle 24 passes through the magnet bore and moves out of the magnet bore, a bridge 25 within the imaging system 22 can support the cradle 24. The rear pedestal 23 includes a cradle traction element 26 and a drive motor 27 thereon The drive motor 27 can drive the cradle traction element 26. The cradle traction element 26 can pass through and protrude out of the magnet bore to couple to the cradle 24, thereby to drive the cradle 24 to move.

The structure of such apparatus has the following problems. The rear pedestal 23 requires a rather larger room. It is also not convenient for the physician to operate on the patient while performing imaging for diagnosis due to the rear pedestal 23.

Since the functions of the rear pedestal 23 are to support the cradle 24 moving into the magnet bore and to drive the cradle 24 to move, a novel cradle drive mechanism must be proposed in order to remove the rear pedestal 23.

There has been a two layered cradle drive mechanism in the prior art, which has an additional intermediate cradle between the table and the cradle. Generally, such two layered cradle drive mechanism employs two drive motors to drive the intermediate cradle and the cradle, respectively, so that the cradle can achieve a large travel range. However, because the mechanism employs two drive motors, this apparatus has high cost and complicated structure; besides, the movement accuracy of the cradle is low.

Japanese Patent Application Publication No. 2010-57700A discloses an improved two layered cradle drive mechanism. As shown in FIG. 2, the cradle drive mechanism includes a drive motor 5, a transmission belt 6, an auxiliary cradle 3 and an endless transmission belt 2. The drive motor 5 can drive the transmission belt 6 by a shaft 9 and two belt wheels 12 fixed on the table base 4. The auxiliary cradle 3 can be supported by a support 16 fixed on the transmission belt 6 and can move with the transmission belt 6. Two belt wheels 13 are fixed on the auxiliary cradle 3. A fastener 14 is fixed on the cradle 1 and is fixed on one side of the endless transmission belt 2, and a fastener 15 is fixed on the table base 4 and is fixed on the other side of the transmission belt 2. Therefore, when the auxiliary cradle 3 is moving, the transmission belt 2 is forced to rotate and drives the cradle 1 to move with it. In the cradle drive mechanism shown in FIG. 2, the cradle 1 can be regarded as an upper layer cradle, and the auxiliary cradle 3 can be regarded as a lower layer cradle, thereby forming the two layered cradle drive mechanism. Though only one drive motor 5 is employed in such a two layered cradle drive mechanism, two transmission belts are employed to drive the upper layer cradle and the lower layer cradle respectively. Because there may be a motion asynchronization between the transmission belts and the belt wheels, the movement accuracy of the cradle 1 is still lower.

Therefore, there is a need for a cradle drive mechanism, a table and a patient imaging and carrying apparatus that can overcome the above mentioned disadvantages.

BRIEF SUMMARY OF THE INVENTION

According to an embodiment of the present invention, a cradle drive mechanism is provided. The cradle drive mechanism comprises a drive motor, an intermediate frame having a first end and a second end opposite the first end, and a screw and nut transmission device disposed between the drive motor and the intermediate frame, Wherein the screw and nut transmission device is driven by the drive motor so as to drive linear reciprocating motion of the intermediate frame. The cradle drive mechanism further comprises a rotating shaft having a first driving wheel and a gear and being mounted at the first end of the intermediate frame, a transmission belt set on the first driving wheel and on a second driving wheel mounted at the second end of the intermediate frame and a rack meshed with the gear so that, during linear reciprocating motion of the intermediate frame, the rack forces the gear to rotate and drive rotation of the first driving wheel, wherein rotation of the first driving Wheel drives rotation of the transmission belt. The cradle drive mechanism further comprises a cradle connector fixed on the transmission belt and configured to connect a cradle and to drive linear reciprocating motion of the cradle.

According to an embodiment of the present invention, a table is provided. The table comprises a table base, a cradle, and a cradle drive mechanism. The cradle drive mechanism comprises a drive motor disposed on the table base, an intermediate frame having a first end and a second end opposite the first end, and a screw and nut transmission device disposed between the drive motor and the intermediate frame, wherein the screw and nut transmission device is driven by the drive motor so as to drive linear reciprocating motion of the intermediate frame. The cradle drive mechanism further comprises a rotating shaft having a first driving wheel and a gear and being mounted at the first end of the intermediate frame, a transmission belt, set on the first driving wheel and on a second driving wheel mounted at the second end of the intermediate frame, and a rack disposed on the table base and meshed with the gear so that, during linear reciprocating motion of the intermediate frame, the rack forces the gear to rotate and drive rotation of the first driving wheel, wherein rotation of the first driving wheel drives rotation of the transmission belt. The cradle drive mechanism further comprises a cradle connector fixed on the transmission belt and configured to connect the cradle to the transmission belt and to drive linear reciprocating motion of the cradle.

BRIEF DESCRIPTION OF DRAWINGS

The present application will be described in more detail in conjunction with embodiments by referring to attached drawings which are not necessarily drawn to scale, wherein.

DETAILED DESCRIPTION TO INVENTION

Details of one or more embodiments of the present application will be explained in the description of the attached drawings and embodiments. Other features, objects and advantages of the present application can become apparent from the description, attached drawings and claims.

In order to solve the technical problem of lower movement accuracy in the cradles of prior art, embodiments of the present application provide a cradle drive mechanism.

The present application will be described in more detail in conjunction with embodiments. Those skilled in the art should understand that these embodiments are just some specific embodiments by way of examples, and are not intended to limit the present application and its scope.

Figure 1:
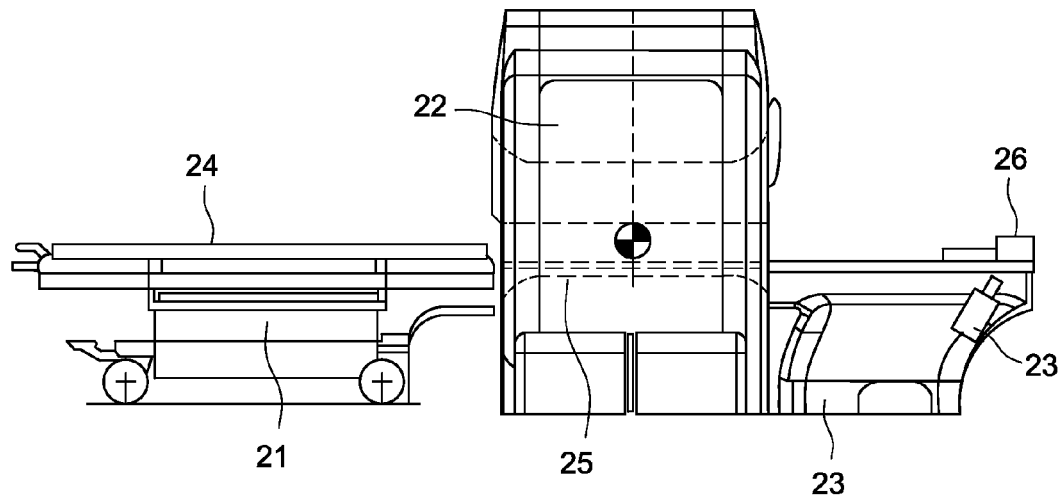
FIG. 1 is a schematic plan view illustrating a patient imaging and carrying apparatus employing a magnetic resonance imaging technique of the prior art.
Figure 2:
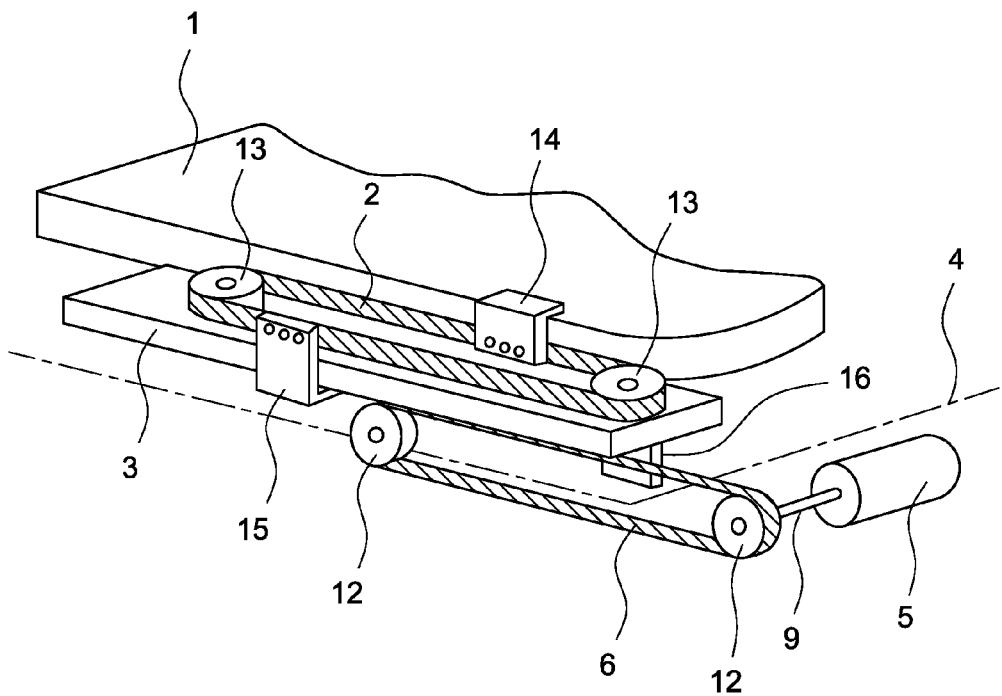
FIG. 2 is a schematic view illustrating a two layered cradle drive mechanism of the prior art.
Figure 3:
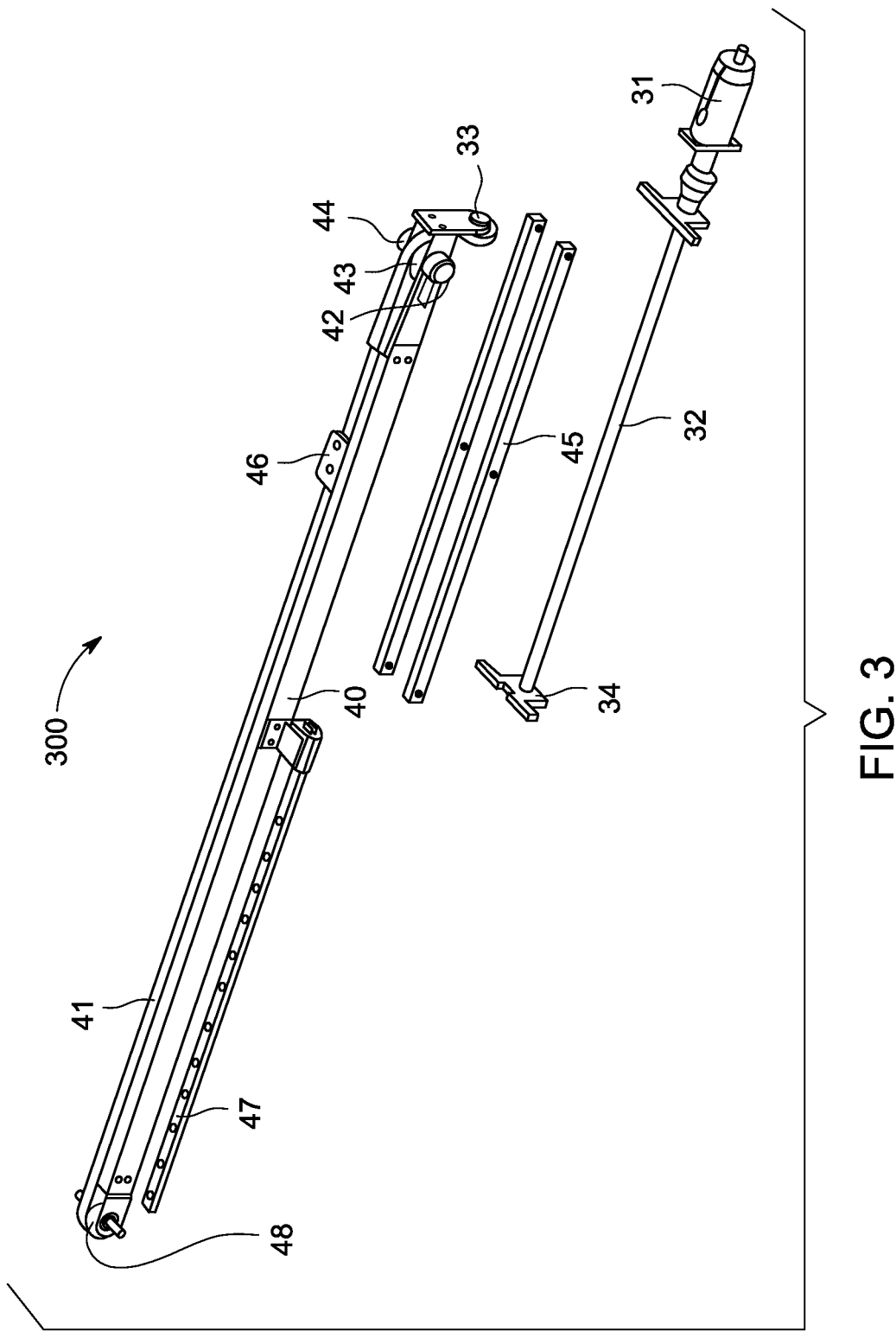
FIG. 3 is a schematic three dimensional exploded view illustrating a cradle drive mechanism according to an embodiment of the present application.

Referring to FIG. 3, a cradle drive mechanism 300 according to an embodiment of the present application is shown. The cradle drive mechanism 300 includes a drive motor 31; a screw and nut transmission device consisting of a screw 32 and a nut 33; an intermediate frame 40; a transmission belt 41; a rotating shaft 42, racks 45; and a cradle connector 46. The rotating shaft 42 includes a first driving wheel 43 and gears 44.

During assembly, the screw and nut transmission device is disposed between the drive motor 31 and the intermediate frame 40. The screw and nut transmission device can be driven by the drive motor 31 so as to drive the intermediate frame 40 to make a linear reciprocating motion. Specifically, the screw 32 of the screw and nut transmission device is fixed on the drive motor 31 and is rotated by the driving of the drive motor 31. The nut 33 is fixed at a first end of the intermediate frame 40 and is meshed with the screw 32. Therefore, according to the principle of relative motion, the clockwise and anticlockwise rotation of the screw 32 can force the nut 33 and the intermediate frame 40 to make the linear reciprocating motion. Of course, the mounted positions of the screw 32 and the nut 33 of the screw and nut transmission device are also interchangeable, which can also drive the intermediate frame 40 to make the linear reciprocating motion. Besides, balls can be provided between the screw 32 and the nut 33 so that a ball screw structure can he formed.

The rotating shaft 42 can be mounted at the first end of the intermediate frame 40. The intermediate frame 40 also has a second end opposite to the first end. The transmission belt 41 is set on the first driving wheel 43 and a second driving wheel 48 mounted at the second end. The racks 45 are meshed with the gears 44 so that when the intermediate frame 40 is making the linear reciprocating motion, the racks 45 can force the gears 44 to rotate and drive the first driving wheel 43 to rotate, The rotation of the first driving wheel 43 can drive the transmission belt 41 to rotate. The cradle connector 46 is fixed on the transmission belt 41. The cradle connector 46 is used to connect a cradle (see the cradle 50 in FIG. 4) and drive the cradle to make the linear reciprocating motion.

According to an embodiment, the drive motor 31 can be an electric motor. The first driving wheel 43 can be a belt wheel so that it can cooperate with the transmission belt 41 to perform the transmission. The first driving wheel 43 may be a synchronous belt wheel, and the transmission belt 41 may be a synchronous belt. The second driving wheel 48 can be a belt wheel. According to one embodiment, the number of the gears 44 is two, and the number of the racks 48 is two. The two gears 44 are fixed at two ends of the rotating shaft 42 respectively. The two racks 45 are located at two sides of the intermediate frame 40 respectively. The two racks 45 are meshed with the two gears 44 respectively so that the driving force exerted on the two sides of the intermediate frame 40 are uniform. The intermediate frame 40 also has a guide 47 mounted thereon which can be used to guide the intermediate frame 40 to make a linear motion. Two ends of the screw 32 can be supported by bearings 34. The rotating shaft 42 can also be disposed on the first end of the intermediate frame 40 by means of a bearing.

Figure 4:
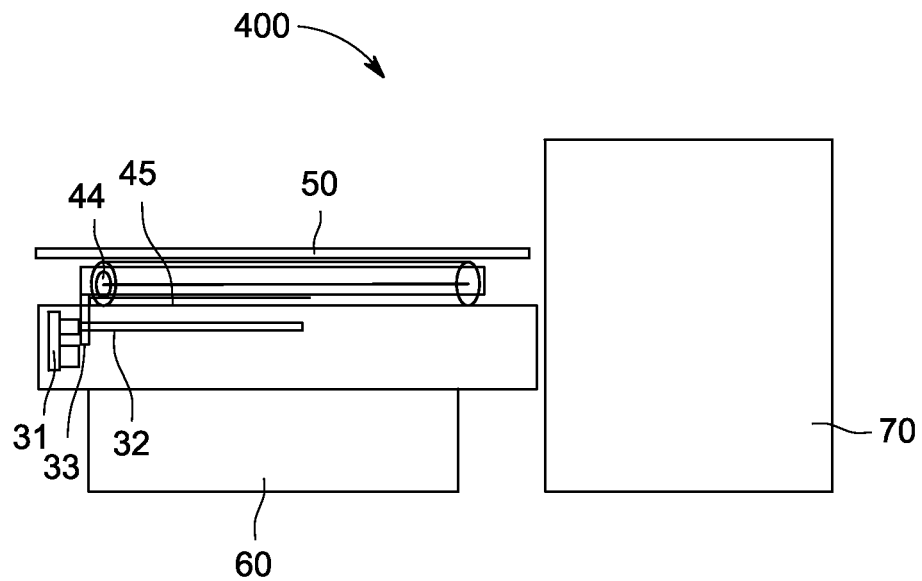
FIG. 4 is a schematic plan view illustrating a patient imaging and carrying apparatus of an embodiment of the present application, which employs the cradle drive mechanism shown in FIG. 3.

Referring to FIG. 4, a patient imaging and carrying apparatus 400 according to an embodiment of the present application is shown. The patient imaging and carrying apparatus 400 employs the cradle drive mechanism 300 shown in FIG. 3 and also includes a cradle 50, a table base 60 and an imaging system 70. The cradle drive mechanism 300, the table base 60 and the cradle 50 constitute a table according to an embodiment of the present application. The cradle 50 is connected to the transmission belt 41 by the above mentioned cradle connector 46. The drive motor 31 and the rack's 45 can be disposed on the table base 60, The above mentioned bearing 34 can be fixed on the table base 60. The above mentioned guide 47 can cooperate with a guide channel fixed on the table base 60. The cradle 50 can enter into the space of the imaging system 70 under the driving of the transmission belt 41.

According to a nembodiment, the imaging system 70 can be a magnetic resonance imaging system. Correspondingly, the space of the imaging system 70 is a magnetic resonance imaging cavity. Of course, the imaging system 70 can also be a computer tomography system, an X-ray imaging system, a positron emission tomography system and the like. Furthermore, the imaging system 70 can also include a cradle support within its space. The cradle support functions to support the cradle 50 when the cradle 50 enters into the space of the imaging system 70.

Figure 5:
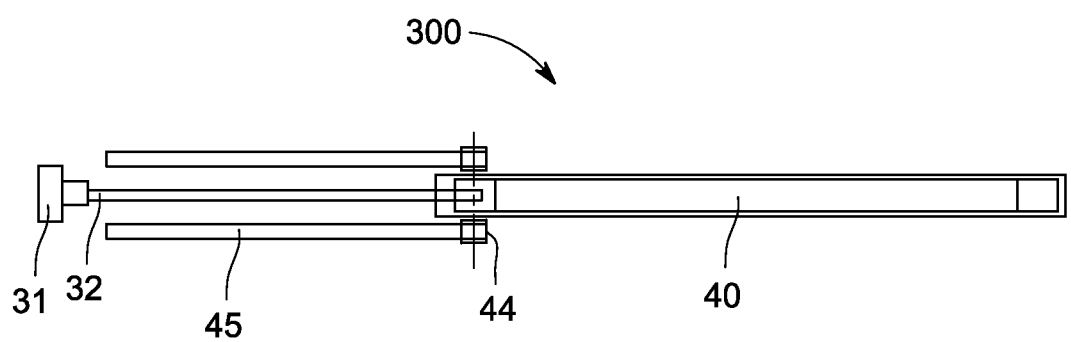
FIG. 5 is a schematic plan view illustrating the cradle drive mechanism shown in FIG. 3 wherein a guide is omitted.

Referring to FIG. 5, a schematic plan view of the cradle drive mechanism 300 shown in FIG. 3 is shown with guide 47 omitted. As can be seen from FIG. 5, the intermediate frame 40 has already moved to the farthest distance by the driving of the screw 32. Correspondingly, when the cradle 50 is fixed on the transmission belt 41, it should also have moved to the farthest distance.

Figure 6:
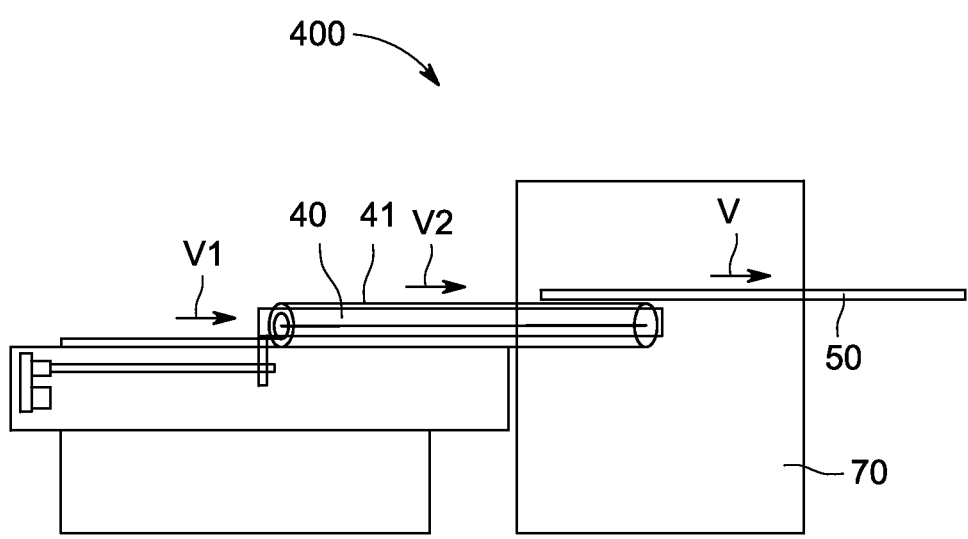
FIG. 6 is a view showing a working status of the patient imaging and carrying apparatus shown in FIG. 4.

Referring to FIG. 6, a view showing a work status of the patient imaging and carrying apparatus 400 shown in FIG. 4 is illustrated. The cradle 50 is carried by the intermediate frame 40 and driven by the transmission belt 41, and passes through and partially protrudes out of the space of the imaging system 70. The velocity V of the motion of the cradle 50 is the sum of the velocity V1 of the intermediate frame 40 and the velocity V2 of the transmission belt 41 relative to the intermediate frame 40. Therefore, the motion of the cradle 50 can be accelerated and, thus, gain a larger travel range. Moreover, the ratio between the velocity V1 and the velocity V2 can be determined by the diameters of the gear 44 and the first driving wheel 43 so that the velocity ratio between the cradle 50 and the intermediate frame 40 can be flexibly adjusted.

According to an embodiment of the present application, the screw and nut transmission device includes a screw and a nut, wherein the screw is mounted on the drive motor and is driven by the drive motor to rotate, and the nut is fixed at the first end of the intermediate frame and is meshed with the screw.

According to another embodiment of the present application, the screw and nut transmission device is a ball screw structure.

According to another embodiment of the present application, the first driving wheel or the second driving wheel is a belt wheel.

According to another embodiment of the present application, the number of gears is two and the number of the racks is two, wherein the two gears are fixed at two ends of the rotating shaft respectively, the two racks are located at two sides of the intermediate frame respectively, and the two racks are meshed with the two gears respectively.

According to another embodiment of the present application, the intermediate frame has a guide fixed thereon which can be used to guide the intermediate frame to make a linear motion.

According to another embodiment of the present application, the imaging system is a magnetic resonance imaging system.

According to another embodiment of the present application, a cradle support is included in the space of the imaging system, wherein the cradle support can be used to support the cradle when the cradle enters into the space of the imaging system.

According to another embodiment of the present invention, a patient imaging and carrying apparatus is provided. The apparatus includes an imaging system and the above mentioned table. The cradle can enter into the space of the imaging system by the driving of the transmission belt.

Compared with the prior art, the cradle drive mechanism, the table and the patient imaging and carrying apparatus of the present application can have the following beneficial results. The movement accuracy of the cradle can be improved by employing the screw and nut transmission device in place of one transmission belt in the prior art to drive the intermediate frame. Besides, since the cradle has a larger travel range, the length of the cradle can be shortened appropriately. In addition, since the cradle and the transmission belt are connected by a cradle connector, such connection can be quickly released under the condition of emergency.

The above description only illustrates the present application exemplarily, and is not intended to restrict the present application, fit should be noted that for those skilled in the art, various improvements, modifications and variations can be made to the present application. However, those improvement, modifications and variations should be construed as within the protective scope of the present application without departing from the spirit of the present application.

What is claimed is:

1. A cradle drive mechanism comprising:
    a drive motor;
    an intermediate frame having a first end and a second end opposite the first end;
    a screw and nut transmission device disposed between the drive motor and the intermediate frame, wherein the screw and nut transmission device is driven by the drive motor so as to drive linear reciprocating motion of the intermediate frame;
    a rotating shaft having a. first driving wheel and a gear and being mounted at the first end of the intermediate frame;
    a transmission belt set on the first driving wheel and on a second driving wheel mounted at the second end of the intermediate frame;
    a rack meshed with the gear so that, during linear reciprocating motion of the intermediate frame, the rack forces the gear to rotate and drive rotation of the first driving wheel, wherein rotation of the first driving wheel drives rotation of the transmission belt; and
    a cradle connector fixed on the transmission belt and configured to connect a cradle and to drive linear reciprocating motion of the cradle.

2. The cradle drive mechanism according to claim 1, wherein the screw and nut transmission device comprises a screw and a nut, wherein the screw is mounted on the drive motor, rotation of the screw being driven by the drive motor, and wherein the nut is fixed at the first end of the intermediate frame and is meshed with the screw.

3. The cradle drive mechanism according to claim 2, wherein the screw and nut transmission device is a ball screw structure.

4. The cradle drive mechanism according to claim 1, wherein at least one of the first driving wheel and the second driving wheel is a belt wheel.

5. The cradle drive mechanism according to claim 1, comprising two gears and two racks, wherein the two gears are fixed at two ends of the rotating shaft respectively, wherein the two racks are located at two sides of the intermediate frame respectively, and wherein the two racks are meshed with the two gears respectively.

6. The cradle drive mechanism according to claim 1, comprising a guide fixed on the intermediate frame, the guide being configured to guide linear reciprocating motion of the intermediate frame.

7. A table comprising:
    a table base;
    a cradle; and
    a cradle drive mechanism comprising:
        a drive motor disposed on the table base;
        an intermediate frame having a first end and a second end opposite the first end;
        a screw and nut transmission device disposed between the drive motor and the intermediate frame, wherein the screw and nut transmission device is driven by the drive motor so as to drive linear reciprocating motion of the intermediate frame;
        a rotating shaft having a first driving wheel and a gear and being mounted at the first end of the intermediate frame;
        a transmission belt set on the first driving wheel and on a second driving wheel mounted at the second end of the intermediate frame;
        a rack disposed on the table base and meshed with the gear so that, during linear reciprocating motion of the intermediate frame, the rack forces the gear to rotate and drive rotation of the first driving wheel, wherein rotation of the first driving wheel drives rotation of the transmission belt; and
        a cradle connector fixed on the transmission belt and configured to connect the cradle to the transmission belt, and to drive linear reciprocating motion of the cradle.

8. A patient imaging and carrying apparatus comprising an imaging system and the table according to claim 7, wherein the cradle can enter into space of the imaging system by the driving of the transmission belt.

9. The patient imaging and carrying apparatus according to claim 8, wherein the imaging system is a magnetic resonance imaging system.

10. The patient imaging and carrying apparatus according to claim 8, comprising a cradle support in the space of the imaging system, wherein the cradle support is configured to support the cradle when the cradle enters into the space of the imaging system.

* * * * *

UNITED STATES PATENT AND TRADEMARK OFFICE
CERTIFICATE OF CORRECTION

| | | |
|---|---|---|
| PATENT NO. | : 8,931,125 B2 | Page 1 of 2 |
| APPLICATION NO. | : 13/628700 | |
| DATED | : January 13, 2015 | |
| INVENTOR(S) | : Fang et al. | |

It is certified that error appears in the above-identified patent and that said Letters Patent is hereby corrected as shown below:

On the Title Page, in Column 1, below Item (65), insert Item -- (30) Foreign Application Priority Data
September 30, 2011 (CN)..............201110312396 --.

On the Title Page, Item (57), under "ABSTRACT", in Column 1, Line 5, delete "rotating," and insert -- rotating --, therefor.

In the Specification

In Column 1, Line 12, delete "diagnosis" and insert -- diagnosis. --, therefor.

In Column 1, Line 33, delete "thereon" and insert -- thereon. --, therefor.

In Column 2, Line 51, delete "belt," and insert -- belt --, therefor.

In Column 3, Line 3, delete "art," and insert -- art; --, therefor.

In Column 3, Line 14, delete "FIG. 3" and insert -- FIG. 3, --, therefor.

In Column 3, Line 38, delete "shaft 42," and insert -- shaft 42; --, therefor.

In Column 3, Line 58, delete "can he" and insert -- can be --, therefor.

In Column 3, Line 66, delete "rotate," and insert -- rotate. --, therefor.

In Column 4, Line 12, delete "racks 48" and insert -- racks 45 --, therefor.

In Column 4, Line 33, delete "rack's" and insert -- racks --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,931,125 B2

In Column 4, Line 34, delete "base 60," and insert -- base 60. --, therefor.

In Column 4, Line 39, delete "nembodiment," and insert -- embodiment, --, therefor.

In Column 5, Line 50, delete "application, fit" and insert -- application. It --, therefor.

In the Claims

In Column 5, Line 66, in Claim 1, delete "a. first" and insert -- a first --, therefor.

In Column 6, Line 62, in Claim 7, delete "belt," and insert -- belt --, therefor.